United States Patent
Kunert et al.

(10) Patent No.: US 8,968,808 B1
(45) Date of Patent: Mar. 3, 2015

(54) PORK BELLY PROCESSING FOR PRE-COOKED BACON

(75) Inventors: Gale F. Kunert, Austin, MN (US); Steven C. Wobschall, Austin, MN (US); John K. Buckles, Austin, MN (US)

(73) Assignee: Hormel Foods Corporation, Austin, MN (US)

(*) Notice: Subject to any disclaimer, the term of this patent is extended or adjusted under 35 U.S.C. 154(b) by 1247 days.

(21) Appl. No.: 12/434,938

(22) Filed: May 4, 2009

(51) Int. Cl.
| | |
|---|---|
| A23L 1/315 | (2006.01) |
| A23L 1/31 | (2006.01) |
| A23C 19/00 | (2006.01) |
| A23B 4/023 | (2006.01) |
| A01K 43/00 | (2006.01) |
| G01N 33/02 | (2006.01) |
| A23G 3/02 | (2006.01) |
| A22C 7/00 | (2006.01) |

(52) U.S. Cl.
USPC ........... 426/281; 426/272; 426/266; 426/231; 426/512; 426/513

(58) Field of Classification Search
USPC .......................................... 426/281, 272, 266
See application file for complete search history.

(56) References Cited

U.S. PATENT DOCUMENTS

| | | | |
|---|---|---|---|
| 1,863,609 A | 6/1932 | Vanderkloot | |
| 1,928,877 A | 10/1933 | Britt et al. | |
| 1,962,877 A * | 6/1934 | Roth et al. | ...... 99/351 |
| 2,158,702 A | 5/1939 | Kipper | |
| 2,431,253 A | 11/1947 | Hoy | |
| 3,385,203 A | 5/1968 | Foldenauer | |
| 3,595,679 A | 7/1971 | Schoch et al. | |
| 3,873,755 A | 3/1975 | McKay | |
| 3,890,451 A | 6/1975 | Keszler | |
| 3,901,981 A | 8/1975 | Draudt | |
| 3,997,672 A | 12/1976 | Stead et al. | |
| 4,029,824 A | 6/1977 | Langen | |
| 4,036,997 A * | 7/1977 | VerBurg | ...... 426/272 |
| 4,038,426 A | 7/1977 | Jespersen et al. | |
| 4,132,810 A | 1/1979 | Knutson | |
| 4,169,161 A | 9/1979 | Leidy et al. | |
| 4,218,492 A | 8/1980 | Stead et al. | |
| 4,409,704 A | 10/1983 | Seiffhart | |
| 4,446,159 A | 5/1984 | Roth | |
| 4,548,108 A | 10/1985 | Dennis | |
| 4,552,768 A | 11/1985 | Olander | |
| 4,603,053 A | 7/1986 | Vegas | |
| 4,657,711 A | 4/1987 | Wigley | |
| 4,731,906 A | 3/1988 | Matthews et al. | |

(Continued)

OTHER PUBLICATIONS

British Meat, Step-by-Step Guides, No. 1. Dry Curing Bacon, (2004).

(Continued)

*Primary Examiner* — Rena L Dye
*Assistant Examiner* — Assaf Zilbering
(74) *Attorney, Agent, or Firm* — IPLM Group, P.A.

(57) ABSTRACT

A method of processing a belly for pre-cooked bacon includes injecting a belly with 1 to 3% by green weight of the belly of a solution comprising water, sodium nitrite, and sodium erythorbate to create an injected belly. The injected belly is tumbled under vacuum with dry ingredients comprising salt, sugar, and dextrose to create a tumbled belly. The tumbled belly is molded in a mold and then frozen in the mold to create a hardened belly. The hardened belly is removed from the mold to create a molded belly. The molded belly is sliced to create belly slices, and the belly slices are cooked.

21 Claims, 4 Drawing Sheets

(56) References Cited

U.S. PATENT DOCUMENTS

| | | | |
|---|---|---|---|
| 4,753,809 A | 6/1988 | Webb | |
| 4,812,320 A | 3/1989 | Ruzek | |
| 4,957,271 A | 9/1990 | Summers et al. | |
| 4,957,756 A * | 9/1990 | Olander et al. | 426/243 |
| 4,960,599 A | 10/1990 | Cozzini et al. | |
| 4,967,652 A | 11/1990 | Mally | |
| 5,052,975 A | 10/1991 | Handel | |
| 5,064,667 A | 11/1991 | Mally | |
| 5,071,666 A | 12/1991 | Handel | |
| 5,132,126 A | 7/1992 | Sinkler et al. | |
| 5,472,722 A | 12/1995 | Burger | |
| 5,520,944 A | 5/1996 | Richardson et al. | |
| 5,567,460 A | 10/1996 | Afman | |
| 5,595,776 A * | 1/1997 | Selz | 426/272 |
| 5,637,342 A | 6/1997 | Brooks et al. | |
| 5,690,989 A | 11/1997 | Clarke et al. | |
| 5,798,133 A | 8/1998 | Kunert | |
| 5,837,305 A | 11/1998 | Kunert | |
| 5,997,925 A | 12/1999 | Wilson et al. | |
| 6,051,264 A | 4/2000 | Afman et al. | |
| 6,214,393 B1 | 4/2001 | Afman et al. | |
| 6,224,927 B1 | 5/2001 | Paulos et al. | |
| 6,391,355 B1 | 5/2002 | Kunert et al. | |
| 6,506,108 B1 | 1/2003 | Jagusch | |
| 6,622,513 B1 * | 9/2003 | Howard | 62/380 |
| 6,669,974 B2 | 12/2003 | Weldy et al. | |
| 6,699,520 B2 | 3/2004 | Paulos et al. | |
| 6,834,576 B2 | 12/2004 | Leitinger | |
| 7,501,140 B2 * | 3/2009 | Gould et al. | 426/513 |
| 2004/0096555 A1 | 5/2004 | Gould et al. | |
| 2006/0165862 A1 * | 7/2006 | Kunert et al. | 426/523 |
| 2007/0110884 A1 | 5/2007 | Kay | |

OTHER PUBLICATIONS

Final Office Action for U.S. Appl. No. 11/043,440 mailed Jan. 30, 2009.

Jay, James. Modern Food Microbiology. New York, Van Nostrand Co., 1970. pp. 31-32.

Komarik, S. et al. Food Products Formulary vol. 1 Meats, Poultry, Fish Shellfish. Westport, CT, AVI Publishing Co., Inc. 1974. pp. 19-23.

Meat Science on Web. http://labs.ansci.uiuc.edu/meatscience/Library/curing.htm, Oct. 28, 2008.

Morton® Salt, Morton® Smoke Flavored Sugar Cure®. http://www.mortonslat.com/products/mearcuring/smkeflavor.html, Nov. 20, 2008.

Non-final Office Action for U.S. Appl. No. 11/043,440 mailed Aug. 29, 2008.

Non-final Office Action for U.S. Appl. No. 11/043,440 mailed Jun. 12, 2009.

Oklahoma State University, "Meat Curing", Oklahoma Cooperative Extension Service ANSI-3994-2, (Apr. 4, 2004).

Romans, et al. The Meat We Eat. The Interstate Printers & Publishers, Inc. Danville, Illinois, 1974. pp. 571-577.

* cited by examiner

PORK BELLY PROCESSING FOR PRE-COOKED BACON

FIELD OF THE INVENTION

The present invention relates to pork belly processing for pre-cooked bacon.

BACKGROUND

Whole pork bellies come from the sides of hogs and are commonly used to make bacon strips. The term "bellies" is used herein to refer to whole bellies or trimmed bellies suitable for making bacon strips.

Federal regulation defines the weight and the yield of bacon products. For uncooked bacon products, cured bellies must have a weight not exceeding the weight of uncured bellies, which is commonly referred to as "green weight". For fully cooked bacon products, cured bellies must have a yield of not more than 40% of the weight of uncured bellies, in other words 60% shrinkage from the green weight of uncured bellies.

Commonly, cure ingredients are injected into bellies with injection needles to create cured bellies, and the cure ingredients must be in solution to prevent clogging of the injection needles. The term "in solution" is used herein to refer to a substantially homogeneous mixture created by a process by which a solid, liquid, or gaseous substance is substantially homogeneously mixed with a liquid. Should the injection needles become clogged, there will be an uneven distribution of the cure ingredients in the bellies.

Most cured bellies are cured using a cure ingredients solution, which comprises dry cure ingredients in a water solution. The cure ingredients solution contains 60 to 70% water by weight of the cure ingredients solution. The bellies are injected with the cure ingredients solution at levels of 8 to 13% by green weight of the bellies so that the injected bellies contain 5 to 9% water by weight of the injected bellies, which adds to the weight of the bellies. To reduce the weight of the injected bellies, to return the injected bellies to their green weight, the injected bellies are commonly cooked slowly in a smokehouse. Cooking the injected bellies in a smokehouse cooks off the water, leaving the cure ingredients behind, and also adds a smoke flavor to the cured bellies.

For fully cooked bacon products, additional weight reduction is necessary after cooking in a smokehouse. To comply with federal regulation, fully cooked bacon products must have a yield of 40% or less to be considered fully cooked. The cured bellies are further cooked using a microwave oven, a conveyor belt having a heat conductive surface, a conveyor belt passing through one or more cooking chambers, or other suitable cooking devices well known in the art to get fully cooked bacon products to 40% yield or less.

For the reasons stated above and for other reasons stated below, which will become apparent to those skilled in the art upon reading and understanding the present specification, there is a need in the art for improved pork belly processing for pre-cooked bacon.

SUMMARY

The above-mentioned problems associated with prior devices are addressed by embodiments of the present invention and will be understood by reading and understanding the present specification. The following summary is made by way of example and not by way of limitation. It is merely provided to aid the reader in understanding some of the aspects of the invention.

In one embodiment method of processing a belly for pre-cooked bacon, a belly is injected with 1 to 3% by weight (green weight) of the belly of a solution comprising water, sodium nitrite, and sodium erythorbate to create an injected belly. The injected belly is tumbled under vacuum with dry ingredients comprising salt, sugar, and dextrose to create a tumbled belly. The tumbled belly is molded in a mold and then frozen in the mold to create a hardened belly. The hardened belly is removed from the mold to create a molded belly. The molded belly is sliced to create belly slices, and the belly slices are cooked.

In one embodiment method of processing a belly for pre-cooked bacon, a belly is injected with 1 to 3% by weight (green weight) of the belly of a solution comprising water, sodium nitrite, and sodium erythorbate to create an injected belly. The injected belly is tumbled under vacuum with dry ingredients comprising salt, sugar, and dextrose to create a tumbled belly. The tumbled belly is placed in a bag to create a bagged belly, and the bagged belly is molded in a mold. The bagged belly is frozen in the mold to create a hardened belly, and the hardened belly is removed from the mold to create a molded belly. The molded belly is removed from the bag and sliced to create belly slices. The belly slices are cooked.

In one embodiment method of processing a belly for pre-cooked bacon, a belly is injected with 1 to 3% by weight (green weight) of the belly of a solution comprising water, sodium nitrite, and sodium erythorbate to create an injected belly. The injected belly is tumbled under vacuum with dry ingredients comprising salt, sugar, and dextrose to create a tumbled belly. The tumbled belly is chilled to create a firmed belly. The firmed belly is molded in a mold and removed from the mold to create a molded belly. The molded belly is frozen to create a hardened belly. The hardened belly is sliced to create belly slices, and the belly slices are cooked.

BRIEF DESCRIPTION OF THE DRAWINGS

The present invention can be more easily understood, and further advantages and uses thereof can be more readily apparent, when considered in view of the detailed description and the following Figures in which.

In accordance with common practice, the various described features are not drawn to scale but are drawn to emphasize specific features relevant to the present invention. Reference characters denote like elements throughout the Figures and the text.

DETAILED DESCRIPTION OF A PREFERRED EMBODIMENT

In the following detailed description, reference is made to the accompanying drawings, which form a part hereof, and in which is shown by way of illustration embodiments in which the inventions may be practiced. These embodiments are described in sufficient detail to enable those skilled in the art to practice the invention, and it is to be understood that other embodiments may be utilized and mechanical changes may be made without departing from the spirit and scope of the present invention. The following detailed description is, therefore, not to be taken in a limiting sense, and the scope of the present invention is defined only by the claims and equivalents thereof.

Generally, embodiments of the present invention include injecting at least one belly with 1 to 3% by weight (green weight) of the at least one belly of pickle solution including water, sodium nitrite, sodium erythorbate, and optionally liquid smoke, and then tumbling the injected belly or bellies under vacuum with dry ingredients such as salt, sugar, dextrose, and optionally liquid smoke. Although a higher percentage by green weight of the at least one belly of pickle solution could be injected into the at least one belly, 1 to 3% by weight (green weight) of the at least one belly of pickle solution is preferred to decrease the cooking time.

Embodiments could also include placing the belly or bellies in a mold, molding the belly or bellies into a shape, and then freezing the belly or bellies in the mold. The belly or bellies are then sliced and cooked to create pre-cooked bacon.

If more than one belly is placed in a mold or form, the bellies could be positioned fat to lean and flank end to rib end relative to the adjacent belly or bellies. Alternatively, a liner or spacer could be positioned between the bellies to mold the bellies more individually.

Figure 1:
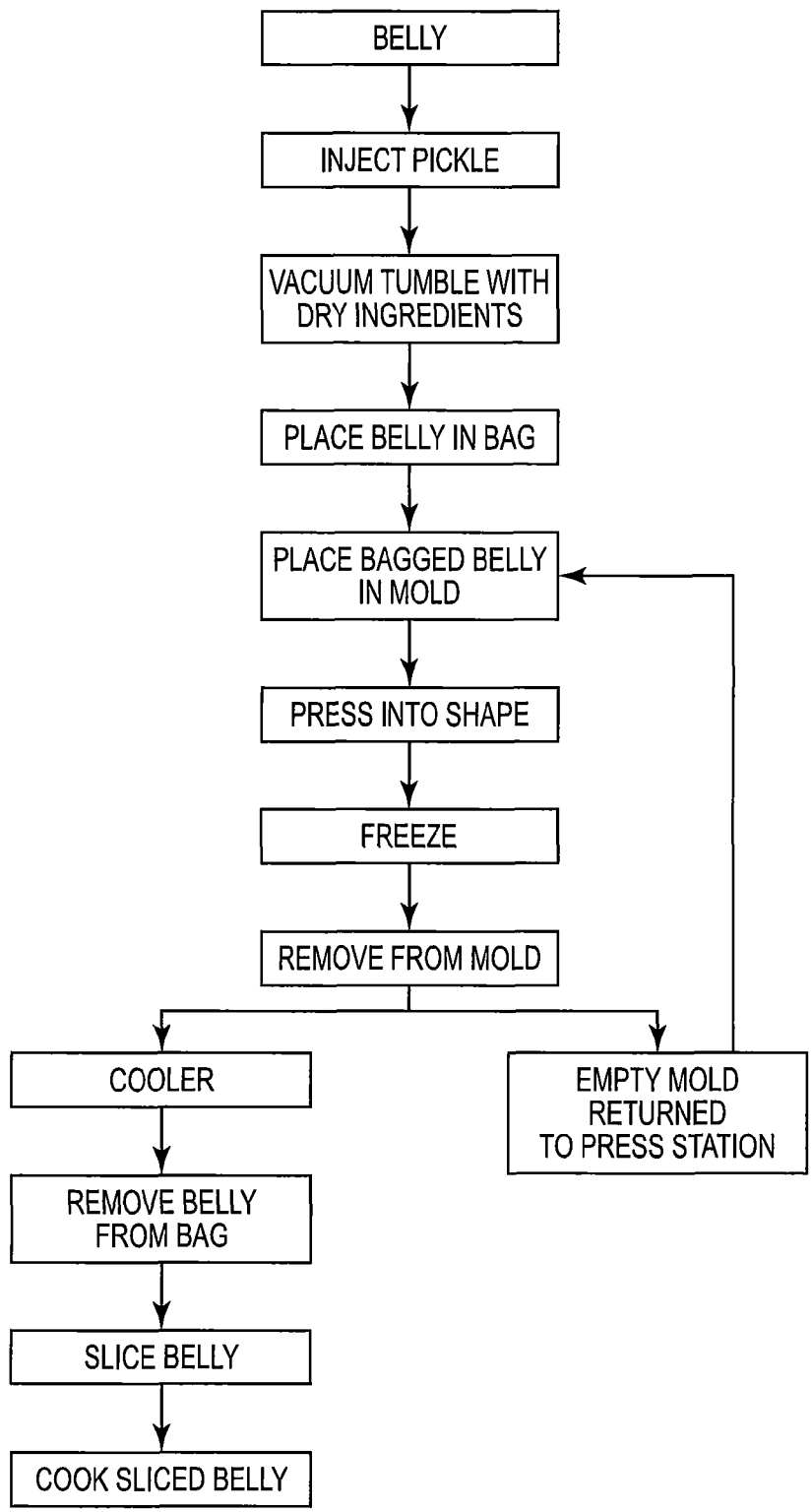
FIG. 1 is a schematic flow diagram of pork belly processing for pre-cooked bacon according to the principles of the present invention.

FIG. 1 shows a schematic flow diagram of pork belly processing for pre-cooked bacon. Although more than one belly could be used, this process is being described using one belly. The belly is injected with 1 to 3% pickle solution of the weight (green weight) of the belly. For example, if the belly is injected with a 2% pickle solution of the green weight of the belly, the 2% pickle solution could include approximately 1.9% water of the green weight of the belly, approximately 120 parts per million ("ppm") sodium nitrite, approximately 550 ppm sodium erythorbate, and optionally liquid smoke. It is important these ingredients go into solution for even distribution of the pickle solution. The sodium nitrite and the sodium erythorbate assist in color development of the belly. An example of a suitable injector is Model No. N50 manufactured by Wolf-tec, Inc., but any suitable injector could be used.

The belly is then vacuum tumbled at approximately 4 to 8 rpm and 25 to 29 inches Mercury ("in. Hg") for at least one hour, preferably 1 to 2 hours, with dry ingredients. For example, the dry ingredients could include approximately 1.5 to 2% salt, 0.2 to 1.5% sugar, 0.2 to 0.7% dextrose, and optionally 0.2 to 1.5% liquid smoke of the green weight of the belly. An example of a suitable vacuum tumbler is Model No. MM-03-TCJ manufactured by CHALLENGE-RMF, INC.

Unlike prior art processes, the belly is not held for 24 to 48 hours. The belly is placed in a plastic bag and then placed in a mold or form in which the belly is molded or formed into a desired shape. Any suitable type of plastic bag or sheet could be used. The mold is preferably a rectangular stainless steel box with a lid and at least one spring-loaded end so that the lid and the at least one spring-loaded end place pressure on the belly. The mold forces the belly into a desired shape for uniformity. The belly's width does not expand, but the belly's length expands. The belly is pressed to a desired thickness. Although any suitable thickness could be used, and the thickness could depend upon the weight or size of the belly, a belly weighing 9 to 11 pounds could be pressed to 1 to 1.25 inches thick.

Figure 3:
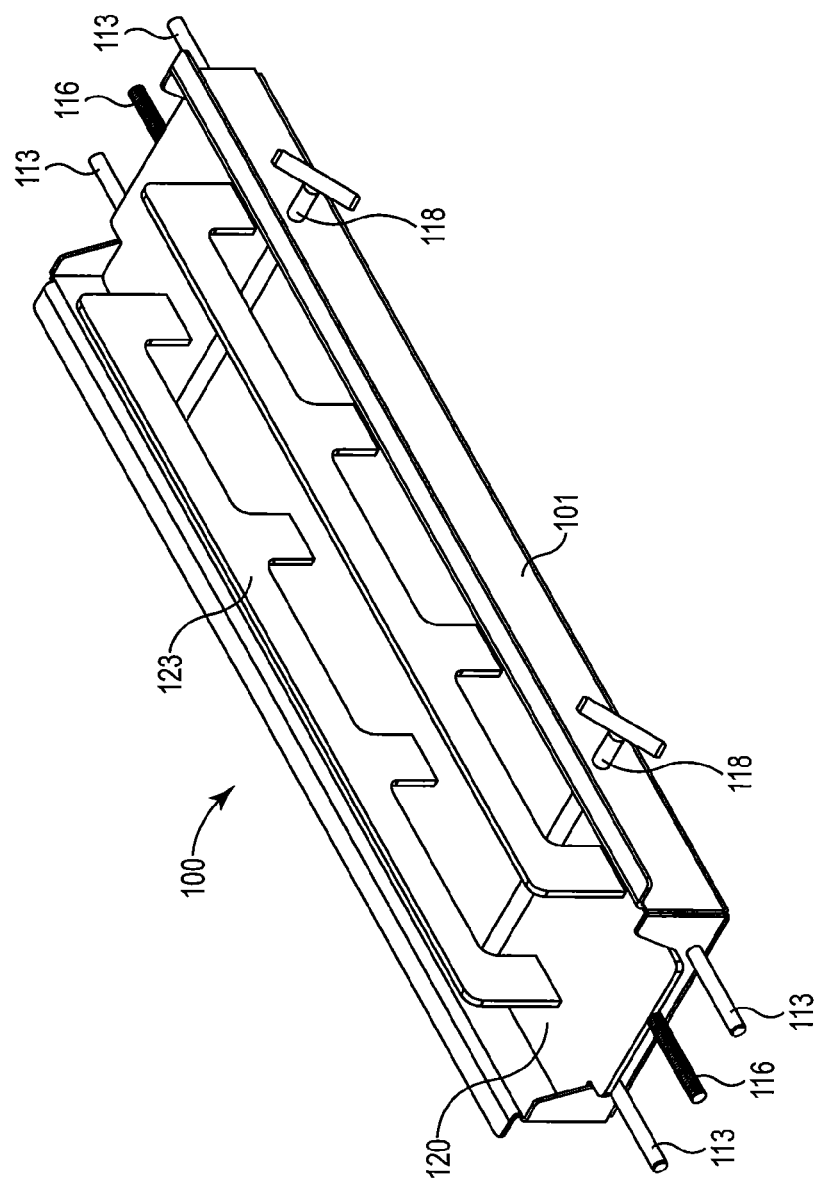
FIG. 3 is a perspective view of a mold constructed in accordance with the principles of the present invention.
Figure 4:
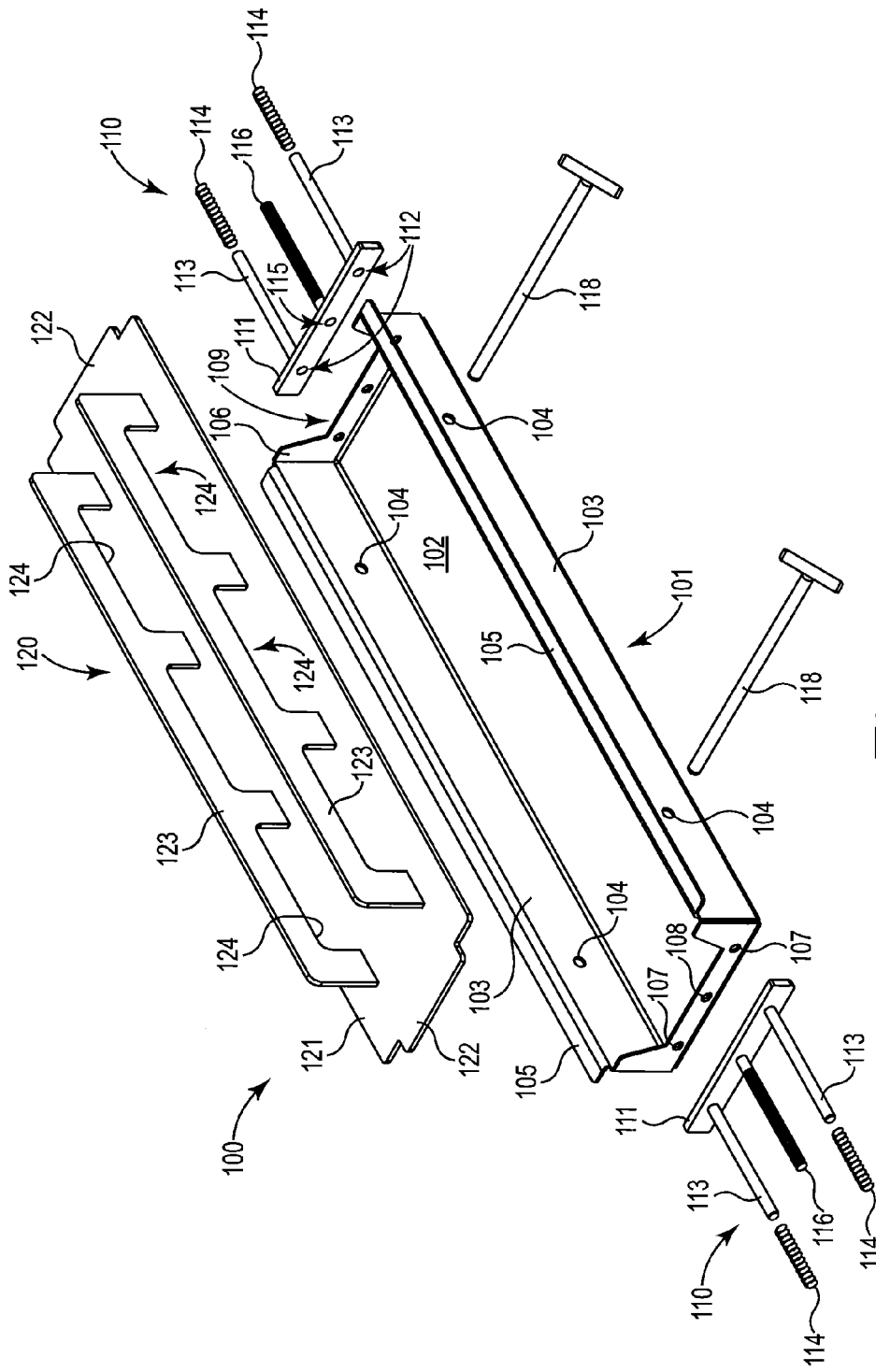
FIG. 4 is an exploded perspective view of the mold shown in FIG. 3.

Although any suitable mold or form could be used, an example of a suitable mold is shown in FIGS. 3 and 4. The mold 100 includes a base portion 101, which is preferably a rectangular box, including a bottom 102, sides 103, and ends 106. The sides 103 extend upward from the bottom 102 and include apertures 104 proximate the ends 106. Flanges 105 extend outward from the sides 103. The ends 106 extend upward from the bottom 102, and each end 106 interconnects the opposing sides 103 and forms a notch 109 proximate the top. The ends 106 include apertures 107 proximate the sides 103 and middle apertures 108 between the apertures 107.

Spring-loaded end portions 110 are operatively connected to the ends 106 and include plate portions 111. The plate portions 111 includes apertures 112 proximate the ends and middle apertures 115 between the apertures 112. Rods 113 extend at least partially into the apertures 112 and are operatively connected to the plate portions 111, and biasing members 114 such as springs are positioned about the rods 113. Rods 116 extend at least partially into the middle apertures 115 and are operatively connected to the plate portions 111. The rods 116 are threaded and nuts (not shown) are configured and arranged to mate with the rods 116. The plate portions 111 are positioned in the base portion 101 and the rods 113 extend through the apertures 107 and the rods 116 extend through the apertures 108. The biasing members 114 are positioned between the plate portions 111 and the ends 106, and the nuts are threaded onto the rods 116 proximate the ends extending outward from the base 101. Thus, the biasing members 114 exert a biasing force on the plate portions 111 to push the plate portions 111 inward. Although two spring-loaded end portions are shown, it is recognized only one spring-loaded end portion could be used.

The lid 120 includes a plate portion 121, which is generally rectangular-shaped corresponding with the shape of the bottom 102 and including extension portions 122 extending outward from the ends. The extension portions 122 extend through the notches 109. Handles 123 extend upward from the plate portion 121 and form openings 124.

The belly (not shown) is placed on the base's bottom 102 between the sides 103 and the plate portions 111. The lid 120 is then positioned on top of the belly, and the extension portions 122 fit within the notches 109. The securing rods 118 are inserted through the apertures 104 on one side 103, through the corresponding apertures in the lid's handles 123, and then through the apertures 104 on the other side 103. The downward force of the lid's plate 121 and the inward force of the spring loaded end portions 110 forces the belly into the desired shape.

The belly is then run through a carbon dioxide tunnel at −90 to −120° F. for 10 to 12 minutes to freeze the belly. The exterior of the belly is frozen to 0° F. or less, and the interior of the belly is frozen to 20 to 28° F. Alternatively, dry ice or any other suitable freezing method could be used to freeze the belly. The belly is removed from the mold or form and stored in a 15 to 20° F. cooler until ready for slicing. When ready for slicing, the belly is removed from the bag, sliced to a desired thickness, and then cooked in a microwave oven to get fully cooked bacon products 40% yield or less. This process makes a uniform belly for slicing and cooking for pre-cooked bacon.

Figure 2:
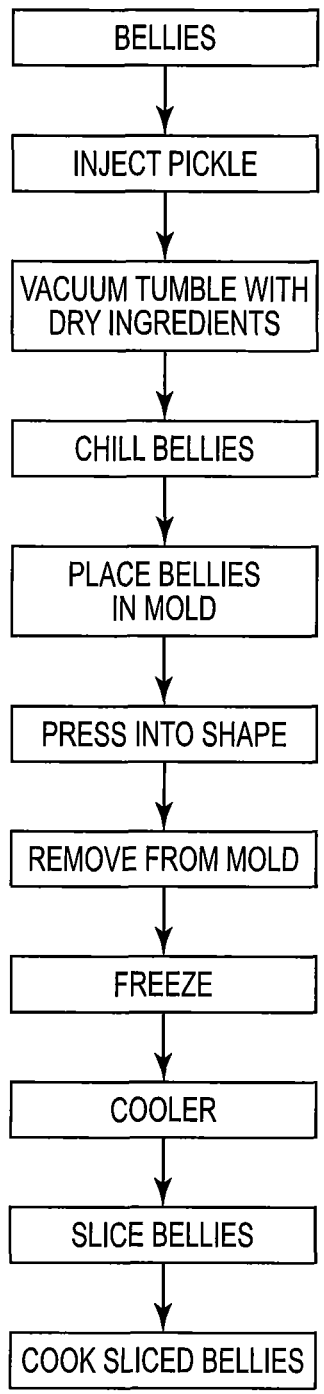
FIG. 2 is a schematic flow diagram of another embodiment pork belly processing for pre-cooked bacon according to the principles of the present invention.

FIG. 2 shows a schematic flow diagram of another embodiment pork belly processing for pre-cooked bacon. Pork bellies, preferably 1 to 4 bellies, are injected with 1 to 3% pickle solution of the weight (green weight) of the bellies. For example, if the belly is injected with a 2% pickle solution of the green weight of the belly, the 2% pickle solution could include approximately 1.9% water of the green weight of the belly, approximately 120 parts per million ("ppm") sodium nitrite, approximately 550 ppm sodium erythorbate, and optionally liquid smoke. It is important these ingredients go into solution for even distribution of the pickle solution. The sodium nitrite and the sodium erythorbate assist in color development of the belly. An example of a suitable injector is Model No. N50 manufactured by Wolf-tec, Inc., but any suitable injector could be used.

The bellies are then vacuum tumbled at approximately 4 to 8 rpm and 25 to 29 in. Hg" for at least one hour, preferably 1 to 2 hours, with dry ingredients. For example, the dry ingredients could include approximately 1.5 to 2% salt, 0.2 to 1.5% sugar, 0.2 to 0.7% dextrose, and optionally 0.2 to 1.5% liquid smoke of the green weight of the bellies. An example of a suitable vacuum tumbler is Model No. MM-03-TCJ manufactured by CHALLENGE-RMF, INC.

Unlike prior art processes, the bellies are not held for 24 to 48 hours. The bellies are individually laid out and then run through a carbon dioxide tunnel at −90 to −120° F. for 3 to 5 minutes to chill and firm up the bellies, commonly referred to as "crust freeze". Alternatively, dry ice or any other suitable chilling method could be used to crust freeze the belly. Preferably, each of the bellies is then positioned in a mold or form in which the belly is molded or formed into a desired shape. The mold is preferably a rectangular stainless steel box, coated with a non-stick coating or lined with a non-stick lining, with a lid and at least one spring-loaded end so that the lid and the at least one spring-loaded end place pressure on the bellies. Although any suitable mold or form could be used, an example of a suitable mold is shown in FIGS. 3 and 4, which is described above. The mold forces the belly into a desired shape for uniformity. The belly's width does not expand, but the belly's length expands. After molding, the bellies are removed from the mold or form.

The bellies are then run through a carbon dioxide tunnel at −90 to −120° F. for 4 to 6 minutes to freeze the bellies. The exterior of the belly is frozen to 0° F. or less, and the interior of the belly is frozen to 20 to 28° F. Alternatively, dry ice or any other suitable freezing method could be used to freeze the belly. The bellies are then stored in a 15 to 20° F. cooler until ready for slicing. When ready for slicing, the bellies are sliced to a desired thickness and then cooked in a microwave oven to get fully cooked bacon products 40% yield or less. This process makes uniform bellies for slicing and cooking for pre-cooked bacon.

Because the sodium nitrite and the sodium erythorbate are injected into the belly or bellies, these ingredients get into the belly or bellies faster to assist in color development. Because of the low level of injection, it is important these ingredients go into solution for even distribution of these ingredients in the pickle solution and in the injected belly or bellies. At this low level of injection, the dry ingredients could not be added to the pickle solution because the dry ingredients would not go into solution and would clog the injection needles. In addition, the low level of injection does not require cooking out extra moisture as in other processes with higher levels of injection. The vacuum tumbling assists in uniform distribution of the low level injection solution. The low level of injection and the vacuum tumbling eliminate the steps of combing and hanging the belly and cooking the belly in a smokehouse. This process includes molding and freezing the belly into the molded shape rather than molding the belly after cooking as in other processes. This allows the belly to be processed faster and more economically.

In addition, the belly is preferably not macerated, which assists in getting a more acceptable product when cooked using a microwave oven. Experience with microwave oven cooking of bacon has shown cuts in raw bellies remain through the process and cause breaks or cuts in the cooked slices. These cuts in the finished products result in uneven or broken slices, which are undesirable, and many are so unacceptable they do not get packaged. Further, putting cuts in bellies with a macerator could result in more char marks, which are undesirable.

The above specification, examples, and data provide a complete description of the manufacture and use of the composition of embodiments of the invention. Since many embodiments of the invention can be made without departing from the spirit and scope of the invention, the invention resides in the claims hereinafter appended.

We claim:

1. A method of processing a belly for pre-cooked bacon, comprising:
    injecting a belly with 1 to 3% by green weight of the belly of a solution comprising water, sodium nitrite, and sodium erythorbate to create an injected belly;
    tumbling the injected belly under vacuum with dry ingredients comprising salt, sugar, and dextrose to create a tumbled belly;
    molding the tumbled belly in a mold without a 24 to 48 hour holding period, the mold forcing the belly into a desired shape;
    freezing the tumbled belly in the mold to create a hardened belly;
    removing the hardened belly from the mold to create a molded belly;
    slicing the molded belly to create belly slices; and
    cooking the belly slices.

2. The method of claim 1, wherein the belly comprises a plurality of bellies.

3. The method of claim 2, wherein the plurality of bellies are arranged fat to lean and flank end to rib end in the mold.

4. The method of claim 1, wherein the solution further comprises liquid smoke.

5. The method of claim 1, wherein the solution is 2% by green weight of the belly and comprises approximately 1.9% water by green weight of the belly, approximately 120 ppm sodium nitrite, and approximately 550 ppm sodium erythorbate.

6. The method of claim 1, wherein the dry ingredients comprise 1.5 to 2% salt, 0.2 to 1.5% sugar, and 0.2 to 0.7% dextrose by green weight of the belly.

7. The method of claim 1, wherein the injected belly is tumbled under vacuum at approximately 4 to 8 rpm and 25 to 29 in. Hg for at least one hour.

8. The method of claim 1, wherein the dry ingredients further comprise liquid smoke.

9. The method of claim 1, further comprising chilling the tumbled belly to create a firmed belly and the firmed belly is molded in the mold.

10. The method of claim 9, wherein the tumbled belly is chilled in a carbon dioxide tunnel at −90 to −120° F. for 3 to 5 minutes to firm the belly.

11. The method of claim 1, wherein the mold comprises a rectangular box with a lid and at least one spring-loaded end, the lid and the at least one spring-loaded end forcing the belly into a desired shape for uniformity.

12. The method of claim 1, wherein an exterior of the belly is frozen to 0° F. or less and an interior of the belly is frozen to 20 to 28° F.

13. The method of claim 1, wherein the tumbled belly is frozen in a carbon dioxide tunnel at −90 to −120° F. for 10 to 12 minutes to harden the belly.

14. The method of claim 1, further comprising placing the molded belly in a cooler at 15 to 20° F. prior to slicing the molded belly to create belly slices.

15. The method of claim 1, wherein the belly slices are cooked in a microwave oven to get fully cooked bacon products 40% yield or less.

16. A method of processing a belly for pre-cooked bacon, comprising:
- injecting a belly with 1 to 3% by green weight of the belly of a solution comprising water, sodium nitrite, and sodium erythorbate to create an injected belly;
- tumbling the injected belly under vacuum with dry ingredients comprising salt, sugar, and dextrose to create a tumbled belly, placing the tumbled belly in a bag to create a bagged belly, molding the bagged belly in a mold without a 24 to 48 hour holding period, the mold forcing the belly into a desired shape;
- freezing the bagged belly in the mold to create a hardened belly;
- removing the hardened belly from the mold to create a molded belly;
- removing the molded belly from the bag;
- slicing the molded belly to create belly slices; and
- cooking the belly slices.

17. The method of claim 16, wherein the solution is 2% by green weight of the belly and comprises approximately 1.9% water by green weight of the belly, approximately 120 ppm sodium nitrite, and approximately 550 ppm sodium erythorbate, and wherein the dry ingredients comprise 1.5 to 2% salt, 0.2 to 1.5% sugar, and 0.2 to 0.7% dextrose by green weight of the belly.

18. The method of claim 16, further comprising placing the molded belly in a cooler at 15 to 20° F. prior to removing the molded belly from the bag.

19. A method of processing a belly for pre-cooked bacon, comprising:
- injecting a belly with 1 to 3% by green weight of the belly of a solution comprising water, sodium nitrite, and sodium erythorbate to create an injected belly;
- tumbling the injected belly under vacuum with dry ingredients comprising salt, sugar, and dextrose to create a tumbled belly;
- chilling the tumbled belly to create a firmed belly;
- molding the firmed belly in a mold without a 24 to 48 hour holding period, the mold forcing the belly into a desired shape;
- removing the firmed belly from the mold to create a molded belly;
- freezing the molded belly to create a hardened belly;
- slicing the hardened belly to create belly slices; and
- cooking the belly slices.

20. The method of claim 19, wherein the solution is 2% by green weight of the belly and comprises approximately 1.9% water by green weight of the belly, approximately 120 ppm sodium nitrite, and approximately 550 ppm sodium erythorbate, and wherein the dry ingredients comprise 1.5 to 2% salt, 0.2 to 1.5% sugar, and 0.2 to 0.7% dextrose by green weight of the belly.

21. The method of claim 19, further comprising placing the hardened belly in a cooler at 15 to 20° F. prior to slicing the hardened belly.

* * * * *